United States Patent [19]

Buske et al.

[11] Patent Number: 5,107,031

[45] Date of Patent: Apr. 21, 1992

[54] PROCES TO RECOVER 4-PHENOXYBIPHENYL

[75] Inventors: Gary R. Buske; Jeffrey M. Marra; Guo-shuh J. Lee, all of Midland, Mich.

[73] Assignee: The Dow Chemical Company, Midland, Mich.

[21] Appl. No.: 452,873

[22] Filed: Dec. 19, 1989

[51] Int. Cl.$^5$ .............................................. C07C 41/40
[52] U.S. Cl. .................................................. 568/635
[58] Field of Search ....................... 568/635, 636, 637

[56] References Cited

U.S. PATENT DOCUMENTS

| | | | |
|---|---|---|---|
| 1,899,257 | 2/1933 | Britton et al. | |
| 2,095,619 | 10/1937 | Stoesser et al. | 260/150 |
| 4,054,533 | 10/1977 | Watson | 252/73 |
| 4,092,364 | 5/1978 | Smith | 260/612 R |
| 4,704,448 | 11/1987 | Brugel | 528/125 |

OTHER PUBLICATIONS

Suzumura, "Synthesis of n-alkyl p-biphenylyl ethers and aryl p-biphenylyl ethers", 35 Bull. Chem. Soc. Japan, pp. 108-111 (1962).

Lüttringhaus et al., 89 Chem. Ber., pp. 463-474 (1956).

Primary Examiner—Alan Siegel
Assistant Examiner—Margaret Argo

[57] ABSTRACT

The invention is a process to recover 4-phenoxybiphenyl from a phenoxybiphenyl mixture which includes at least 30% by weight of 4-phenoxybiphenyl, the balance being 2-phenoxybiphenyl, 3-phenoxybiphenyl and a minor amount of other compounds. The process involves recrystallizing 4-phenoxybiphenyl as a solid in a single recrystallization step from a solution formed from the mixture and an alcohol solvent. The recovered solid has a 4-phenoxybiphenyl content of at least about 85% by weight of recovered solid and a yield of at least 40% based on the amount of 4-phenoxybiphenyl in the mixture.

19 Claims, No Drawings

PROCES TO RECOVER 4-PHENOXYBIPHENYL

BACKGROUND OF THE INVENTION

The invention concerns a process to recover 4-phenoxybiphenyl from mixtures containing the compound and its isomers, 3-phenoxybiphenyl and 2-phenoxybiphenyl.

Phenoxybiphenyls are produced as byproducts from industrial processes that produce diphenyl ether. Diphenyl ether is produced by the caustic hydrolysis of chlorobenzene, as is generally taught by Smith, *Caustic Hydrolysis of Chlorobenzene to Diphenyl Oxide*, U.S. Pat. No. 4,092,364 (May 30, 1978), the teachings of which are incorporated herein by reference. A byproduct stream from the process contains a major amount of the 2-phenoxybiphenyl isomer, with smaller proportions of the 4-phenoxybiphenyl and 3-phenoxybiphenyl isomers, 2,6-diphenylphenol and a variety of other compounds.

Phenoxybiphenyls are commercially useful as monomer precursors in the production of polyetherketone resins. For example, Brugel, *Copolyetherketones*, U.S. Pat. No. 4,704,448 (Nov. 3, 1987), teaches the preparation of polyetherketones by contacting diphenyl ethers with diacid halides in a Friedel-Crafts synthesis. The 4-phenoxybiphenyl structure is useful in preparing acceptable monomers. See, Brugel at column 3, lines 23-24. It is preferable to use a highly pure form of the 4-phenoxybiphenyl isomer when preparing the monomers.

Distillation of the byproduct mixture to obtain a highly pure 4-phenoxybiphenyl product is not practical. The three isomers and 2,6-diphenylphenol have similar chemical structures, and thus, it is not surprising that the compounds have roughly equivalent boiling points. Due to the close boiling points, it is not practical to recover the 4-phenoxybiphenyl isomer in a highly pure form by use of a distillation column.

Similarly, persons skilled in the art would expect roughly equivalent solubilities for the isomers in various solvents, as is the case with available physical properties such as boiling points. Therefore, one would also anticipate difficulty in attempting to recrystallize 4-phenoxybiphenyl from a mixture of the three isomers.

It is known in the art that phenoxybiphenyl compounds can be purified by recrystallization from ethanol. See, Stoesser et al., *Aryl Oxides*, U.S. Pat. No. 2,095,619 (Oct. 12, 1937) at Examples 1-3. However, Stoesser et al. do not teach recovery of 4-phenoxybiphenyl by recrystallization from a mixture that includes its isomers. It is clear that Stoesser et al. merely purify the product of a reaction designed to produce one isomer.

Therefore, it is desirable to discover a process to economically and easily recover a highly pure 4-phenpxybiphenyl solid from mixtures containing this compound and its isomers.

SUMMARY OF THE INVENTION

The present invention is a process to recover 4-phenoxybiphenyl from a phenoxybiphenyl mixture comprising at least about 30% by weight of 4-phenoxybiphenyl and up to about 70% by weight of its 2-phenoxybiphenyl and 3-phenoxybiphenyl isomers. The process comprises recovering, in a single recrystallization step from a solution containing the phenoxybiphenyl mixture and an alcohol solvent, a solid having an increased 4-phenoxybiphenyl content relative to the phenoxybiphenyl mixture, the content being at least about 85% by weight of recovered solid.

DETAILED DESCRIPTION OF THE INVENTION

Recrystallization from a solution is generally discussed by Perry et al., "Chemical Engineers'Handbook" 5th ed., pps. 17-8 to 17-18 (McGraw-Hill 1973), the teachings of which are incorporated herein by reference. In general, a compound may be recovered from an impure mixture by dissolution of the mixture in a solvent in which the desired compound is less soluble than other components of the mixture. The resulting solution is cooled and beneficially results in crystals of the desired compound which exhibit improved purity. The filtrate, i.e., the remaining solvent and solutes, may be recycled to improve overall yield of the desired compound, as is known by those familiar with the art of recrystallization.

A detailed description of phenoxybiphenyl mixtures processed according to the present invention is not necessary. as both the compounds and their mixtures are known and commercially available. A general description of the compounds and their mixtures appears in Watson, *Heat Transfer Fluids Having Low Freeze Points*, U.S. Pat. No. 4,054,533 (Oct. 18, 1977), the teachings of which are incorporated herein by reference.

In practicing the present invention, the concentration of the desired 4-phenoxybiphenyl isomer in the phenoxybiphenyl mixture is suitably at least about 30% by weight of the mixture. The balance of the mixture, or up to about 70% by weight, comprises the 2-phenoxybiphenyl and 3-phenoxybiphenyl isomers. Recrystallization of mixtures having concentrations less than the 30% by weight threshold amount may produce a solid having a 4-phenoxybiphenyl content that is too impure for use in commercial processes. such as a process for producing monomers used in synthesis of polyetherketone resins. The term "too impure" means that the recovered solid has a 4-phenoxybiphenyl purity of less than about 85% by weight of the recovered solid. Mixtures with 4-phenoxybiphenyl concentrations in excess of 30% may be recrystallized in a single step to produce a solid having an increased 4-phenoxybiphenyl content relative to the mixture. The 4-phenoxybiphenyl content of the recovered solid is at least about 85% by weight.

Commercially available phenoxybiphenyl mixtures typically contain the 4-phenoxybiphenyl isomer at a concentration of from about 24% to about 26% by weight of the mixture. It is therefore necessary to increase the concentration of the isomer to at least about 30% by weight. The concentration may be increased by any convenient method. such as distillation.

Phenoxybiphenyl mixtures may contain other compounds which are typically present in commercially available mixtures. The manufacturing processes from which the mixtures are derived form minor amounts, i.e., less than about 20% by weight of the mixture, of other compounds such as diphenyl ether, 2,6-diphenylphenol and 2,4-diphenylphenol. Additional examples of the other compounds are given in U.S. Pat. No. 4,054,533 at column 1, line 54 to column 3, line 30. The concentration of the other compounds is desirably no more than about 20% by weight and preferably no more than about 15% by weight.

In practicing the invention, suitable solvents used for recrystallization are lower alcohols. Suitable lower alcohols have no greater than about ten carbon atoms and preferably no greater than about four carbon atoms. Examples of suitable alcohol solvents are methanol, ethanol, 1-propanol, 2-propanol, 1-butanol, 2-butanol. 2-methyl-2-propanol, 2-methyl-1-propanol, 1-pentanol, cyclohexanol. 2-ethyl-1-hexanol and so on. Preferred solvents are methanol, ethanol, 1-propanol and 2-propanol. Solvents may be used singly or in combination. The most preferred solvent is 2-propanol, which provides good results with the use of a moderate amount of solvent. Methanol and ethanol work well, but the phenoxybiphenyl compounds are not as soluble therein and, therefore, they require the use of a larger amount of solvent to achieve a similar result.

The amount of solvent used in recovering the 4-phenoxybiphenyl isomer will vary, the amount being dependent on the choice of solvent. If 2-propanol is chosen, a weight ratio of 2-propanol to the phenoxybiphenyl mixture is suitably from about 2.0 to about 12.0. A weight ratio less than about 2.0 is undesired, because the mixture is recovered as an impure oil. Operation at weight ratios in excess of 12.0 is undesired, because the large excess of solvent does not allow crystal formation without cooling to temperatures of about 0° C. or lower. It is preferred to operate at a weight ratio of about 2.5 to about 6.5, as operation within this range produces good results with respect to yield and purity of the desired isomer when recrystallizing 4-phenoxybiphenyl from solution at a temperature of about 20-35° C. The preferred range also minimizes the amount of solvent employed.

The use of ethanol and methanol as a solvent requires generally a greater amount of solvent to achieve similar results. If ethanol is chosen as the solvent, the weight ratio is suitably from about 4.0 to about 15.0, with a preferred ratio of from about 5.0 to about 8.0. If methanol is chosen as the solvent, the weight ratio is suitably from about 5.0 to about 20.0, with a preferred ratio of from about 6.0 to about 10.0.

Dissolution of the phenoxybiphenyl mixtures into a solvent may be achieved by any convenient method. A suitable method is to maintain the mixture and an alcohol solvent at a temperature sufficient to promote dissolution. For example, a temperature of from about 50° C. to about the boiling point of the alcohol solvent will generally suffice to dissolve the mixture into the alcohol solvent. The temperature at which the mixtures will dissolve depends upon the type and amount of solvent employed. An effective temperature may be ascertained without undue experimentation by those skilled in the art.

After dissolution, the resulting solution is cooled to a temperature which promotes 4-phenoxybiphenyl solid formation. A beneficial cooling rate is achieved by allowing the solution to cool to room temperature over a period of from about one hour to about four hours. As those skilled in the art can appreciate. a slower cooling rate will increase the purity of the resulting solid. If the solution is cooled too quickly, such as quenching a flask containing the warm solution in an ice bath, the mixture may separate from the solution as an impure oil. The rate of cooling will depend upon the purity desired and solvent employed, but a suitable rate may be determined by those skilled in the art without undue experimentation.

The temperature at which crystalline solids form will depend upon the choice and amount of solvent employed. For example, solids form at a temperature of from about 30° C. to about 35° C. when using a 2-propanol solvent at a weight ratio of 2-propanol to the phenoxybiphenyl mixture of about 3.5. Increasing this weight ratio to about 9.5 leads to cystallization at temperatures below about 20° C.. Generally, cooling the resulting solutions to a temperature of from about −5° C. to about 35° C. is sufficient to produce a highly pure 4-phenoxybiphenyl solid. As used herein, the term "highly pure" means that the solids obtained by recrystallization contain 4-phenoxybiphenyl of at least about 85% by weight of recovered solid. It is economically desirable, and therefore preferred, to conduct recrystallization at a temperature above about 20° C., in order to avoid use of refrigeration for cooling purposes.

After solid formation, the 4-phenoxybiphenyl product may be isolated by any convenient method. such as filtering the solid from the solvent and residual solutes, washing the solid to rinse any remaining solvent therefrom, and drying the solid to obtain a final product.

The present invention recovers a 4-phenoxybiphenyl-biphenyl solid at a high yield having an increased 4-phenoxybiphenyl isomer content relative to the phenoxybiphenyl mixture. As used herein, the term "high yield" means that the amount of the 4-phenoxybiphenyl isomer recovered is at least about 40% based upon the amount of 4-phenoxybiphenyl present in the mixture. The yield is desirably at least about 44% and preferably at least about 50%. It is possible to have yields below 40%, but it is generally undesirable to do so, due to the uneconomical loss of starting material in the filtrate. The content of 4-phenoxybiphenyl in the solid is suitably at least about 85% by weight, desirably at least about 90% by weight and preferably at least about 95% by weight.

The recovered 4-phenoxybiphenyl solid may be used to prepare acceptable monomers for producing polyetherketone resins.

SPECIFIC EMBODIMENTS OF THE INVENTION

The following examples and comparative example are given to illustrate specific embodiments of the invention. These examples should not be construed, by implication or otherwise, as limiting the scope thereof. All parts and percentages are by weight and all temperatures are in degrees Celsius (° C.) unless otherwise indicated.

EXAMPLE 1

A commercially available mixture of phenoxybiphenyls produced by the Dow Chemical Company and sold as technical grade biphenylyl phenyl ethers (referred to herein as "tech-BIPPE") typically displays the following composition, in terms of area percentages as determined by capillary gas chromatography:

0.4% diphenyl ether;
56.2% 2-phenoxybiphenyl;
1.5% 3-phenoxybiphenyl;
27.5% 4-phenoxybiphenyl;
6.1% 2,6-diphenylphenol; and
8.3% other compounds.

It is believed that the area percentage for each compound is equivalent to its actual weight percentage, since the mixture is a distillate of structurally similar compounds. Due to the fact that the tech-BIPPE mixture is produced in commercial scale equipment, it should be understood that its composition fluctuates.

Operation of a 25 tray batch distillation column used to produce the tech-BIFFE mixture is altered to increase the concentration of the 4-phenoxybiphenyl isomer. A portion of the lower boiling components is initially removed by distillation to increase the concentration of the higher boiling 4-phenoxybiphenyl isomer in the column. A fraction boiling at a temperature of about 230°–232° C. and a pressure of about 20 millimeters of Hg is collected from an overhead product line. The fraction is analyzed by capillary gas chromatography and displays the following composition, in terms of area percentages as determined by capillary gas chromatography:

1.8% diphenyl ether;
37.9% 2-phenoxybiphenyl;
5.2% 3-phenoxybiphenyl;
48.9% 4-phenoxybiphenyl;
2.4% 2,6-diphenylphenol; and
3.8% other compounds.

The percentage of diphenyl ether in the above-described fraction is higher than expected, which suggests inadvertent contamination, possibly by a residual amount of diphenyl ether present in a container used to collect the sample. The belief is based upon comparison of the concentration of diphenyl ether in the fraction versus the concentration of diphenyl ether normally present in the tech-BIPPE mixture.

A solution is prepared by mixing and heating in a flask 650 grams of the phenoxybiphenyl mixture described in the two preceding paragraphs with 2170 grams of 2-propanol. The weight ratio of 2-propanol to the phenoxybiphenyl mixture is about 3.3. The flask is heated by use of a steam bath to a temperature of about 82° C., i.e., the boiling point of 2-propanol, and maintained at that temperature until the phenoxybiphenyl mixture is dissolved. The resulting solution is then slowly cooled to a temperature of about 18° C. by placing the warm flask and its contents on a laboratory bench top and allowing them to cool to room temperature over a period of approximately four hours. A large amount of solids form at a temperature of about 35° C.. After cooling, the solids are filtered; washed with about 50 grams of cold 2-propanol. i.e., 2-propanol maintained at a temperature of about 10° C.; and finally vacuum dried in an oven maintained at a temperature of about 25° C..

The product is 220 grams of a solid which assays, in terms of area percentage as determined by capillary gas chromatograpy, as 95.0% 4-phenoxybiphenyl. The yield of 4-phenoxybiphenyl from the mixture is 65.8% based upon the amount of 4-phenoxybiphenyl charged to the flask prior to dissolution and recrystallization.

EXAMPLE 2

The procedure of Example 1 is substantially repeated, except for use of a different solvent, as well as reduced proportions of the phenoxybiphenyl mixture and solvent. A solution is formed as in Example 1 by adding 2.0 grams of the phenoxybiphenyl mixture to a flask containing about 15.8 grams of methanol, thereby giving a weight ratio of methanol to the phenoxybiphenyl mixture of about 7.9. The flask and its contents are heated to about 65° C., i.e.. the boiling point of methanol, and maintained at that temperature until the phenoxybiphenyl mixture is dissolved. The resulting solution is allowed to cool slowly, as in Example 1, to a temperature of about 20° C. which results in formation of solids. The solids are filtered and dried to produce 0.45 grams of a solid which assays, in terms of an area percentage as determined by capillary gas chromatography, as 96.8% 4-phenoxybiphenyl. The yield of 4-phenoxybiphenyl is 44.5% based upon the amount of 4-phenoxybiphenyl charged to the flask.

EXAMPLE 3

The procedure of Example 2 is substantially repeated except for the use of ethanol, rather than methanol, as the solvent. A solution is formed by adding 2.0 grams of the phenoxybiphenyl mixture to a flask containing about 11.9 grams of ethanol, thereby giving a weight ratio of ethanol to the phenoxybiphenyl mixture of about 5.9. The contents of the flask are heated to a temperature of about 78° C., i.e., the boiling point of ethanol. and maintained at that temperature until the phenoxybiphenyl mixture is dissolved. The resulting solution is allowed to cool slowly to a temperature of about 20° C. as in Example 1. At this point, no solids are observed in the solution. The contents of the flask are then cooled to about 0° C. by placing the flask in an ice bath. A large amount of solids are observed to form in the solution. The solids are filtered and dried to produce 0.59 grams of a solid which assays,. in terms of an area percentage as determined by capillary gas chromatography, as 96.7% 4-phenoxybiphenyl. The yield of 4-phenoxybiphenyl is 58.3% based upon the amount of 4-phenoxybiphenyl charged to the flask.

EXAMPLE 4

The procedure of Example 1 is substantially repeated using a phenoxybiphenyl mixture having a reduced concentration of the 4-phenoxybiphenyl isomer. The phenoxybiphenyl mixture used in this example has the following composition, In terms of area percentages as determined by capillary gas chromatography:

56.3% 2-phenoxybiphenyl;
4.4% 3-phenoxybiphenyl;
32.8% 4-phenoxybiphenyl;
1.2% 2,6-diphenylphenol; and
5.3% other impurities.

The mixture is obtained by distillation as in Example 1. The mixture is a fraction boiling at a temperature of about 230–232° C. and a pressure of about 20 millimeters of Hg. This fraction is sampled from the overhead product line prior to collection of the fraction previously described in Example 1.

A solution is formed by adding 8 grams of the phenoxybiphenyl mixture described in the preceding paragraph and 75.4 grams of 2-propanol to a flask and heating the contents thereof to a temperature of about 82° C., i.e., the boiling point of 2-propanol, and maintaining the temperature until the mixture is dissolved. The weight ratio of 2-propanol to the phenoxybiphenyl mixture is about 9.4. The resulting solution is slowly cooled to a temperature of about 20° C. as in Example 1. At this point, no solids are observed in the solution. The solution is cooled to a temperature of about 0° C. by placing the flask into an ice water bath. Solids are observed to form in the solution. The solids are filtered and dried as in Example 1. The product is 1.44 grams of a solid which assays, in terms of area percentage as determined by capillary gas chromatography, as 97.8% 4-phenoxybiphenyl. The yield of 4-phenoxybiphenyl is 53.7% based upon the amount of 4-phenoxybiphenyl charged to the flask.

COMPARATIVE EXAMPLE A

The procedure of Example 1 is substantially repeated using a phenoxybiphenyl mixture having a reduced concentration of the 4-phenoxybiphenyl isomer. A solution is formed by mixing 100 grams of the tech-BIPPE mixture previously described in Example 1 with 785 grams of 2-propanol in a flask and heating as in Example 1. The weight ratio of 2-propanol to the mixture is about 7.85. The resulting solution is cooled to about 20° C. as in Example 1 without any solids forming in the solution. The solution is cooled in a refrigerator to a temperature of about 3° C. and solids are observed to form in the solution. The solids are filtered; washed with about 78.5 grams of cold 2-propanol, i.e., 2-propanol at a temperature of about 3° C.; and vacuum dried as in Example 1. The product is 26.5 grams of a solid which assays. in terms of an area percentage as determined by capillary gas chromatography, as 53.6% 4-phenoxybiphenyl. The yield of 4-phenoxybiphenyl is 51.6 based upon the amount of 4-phenoxybiphenyl charged to the flask prior to dissolution and recrystallization.

Comparative Example A, in conjunction with Example 4, illustrates that the concentration of the 4-phenoxybiphenyl isomer must be greater than about 30% by weight of the phenoxybiphenyl mixture to recover a highly pure 4-phenoxybiphenyl product.

Similar results are obtained with other alcohol solvents and process variations as previously disclosed herein.

What is claimed is:

1. A process for recovering 4-phenoxybiphenyl from a phenoxybiphenyl mixture comprising at least about 30% by weight of 4-phenoxybiphenyl and up to about 70% by weight of its 2-phenoxybiphenyl and 3-phenoxybiphenyl isomers, the process comprising recovering, in a single recrystallization step from a solution containing the phenoxybiphenyl mixture and an alcohol solvent, a solid having an increased 4-phenoxybiphenyl content relative to the phenoxybiphenyl mixture, the 4-phenoxybiphenyl content being at least about 85% by weight of recovered solid.

2. The process of claim 1 wherein the alcohol solvent has a carbon atom content of no greater than about 10.

3. The process of claim 1 wherein the alcohol solvent is selected from the group consisting of methanol, ethanol, 1-propanol, 2-propanol, 2-methyl-2-propanol, 2-methyl-1-propanol, 1-butanol, 2-butanol, 1-pentanol, cyclohexanol, 2-ethyl-1-hexanol and mixtures thereof.

4. The process of claim 1 wherein during recrystallization the solution is cooled to a temperature of from about −5° C. to about 35° C..

5. The process of claim 1 wherein during recrystallization the solution is cooled to a temperature of from about 20° C. to about 35° C..

6. The process of claim 1 wherein during recrystallization the solution is cooled at a rate which prevents formation of an impure oil.

7. The process of claim 1 wherein the 4-phenoxybiphenyl solid recovered has a purity of at least about 90% by weight.

8. The process of claim 1 wherein the 4-phenoxybiphenyl solid recovered has a purity of at least about 95% by weight.

9. The process of claim 1 which includes a yield of 4-phenoxybiphenyl of at least 40%.

10. The process of claim 1 which includes a yield of 4-phenoxybiphenyl of at least 50%.

11. The process of claim 1 wherein the alcohol solvent is 2-propanol.

12. The process of claim 11 wherein 2-propanol is present at a weight ratio of 2-propanol to the phenoxybiphenyl mixture of from about 2.0 to about 12.0.

13. The process of claim 11 wherein 2-propanol is present at a weight ratio of 2-propanol to the xybiphenyl mixture of from about 2.5 about 6.5.

14. The process of claim 1 wherein the alcohol solvent is ethanol.

15. The process of claim 14 wherein ethanol is present at a weight ratio of ethanol to the phenoxybiphenyl mixture of from about 4.0 to about 15.0.

16. The process of claim 14 wherein ethanol is present at a weight ratio of ethanol to the phenoxybiphenyl mixture of from about 5.0 to about 8.0.

17. The process of claim 1 wherein the alcohol solvent is methanol.

18. The process of claim 17 wherein methanol is present at a weight ratio of methanol to the phenoxybiphenyl mixture of from about 5.0 to about 20.0.

19. The process of claim 17 wherein methanol is present at a weight ratio of methanol to the phenoxybiphenyl mixture of from about 6.0 to about 10.0.

* * * * *

UNITED STATES PATENT AND TRADEMARK OFFICE
CERTIFICATE OF CORRECTION

PATENT NO. : 5,107,031
DATED : April 21, 1992
INVENTOR(S) : Gary R. Buske, et. al.

It is certified that error appears in the above-indentified patent and that said Letters Patent is hereby corrected as shown below:

On the Title page, item [54], col. 1, line 1, "PROCES" should read -- PROCESS--.

Column 8, lines 28-29, in claim 13, "xybiphe-nyl" should read -- phenoxybiphenyl--.

Signed and Sealed this

Seventeenth Day of August, 1993

Attest:

BRUCE LEHMAN

*Attesting Officer*   *Commissioner of Patents and Trademarks*